United States Patent [19]

Schut et al.

[11] 4,140,769

[45] Feb. 20, 1979

[54] 3-SUBSTITUTED SALICYLAMIDES

[75] Inventors: Robert N. Schut, Edwardsburg, Mich.; Harold E. Hartzler, Goshen, Ind.; Edgar O. Snoke; John W. Van Dyke, Jr., both of Elkhart, Ind.

[73] Assignee: Miles Laboratories, Inc., Elkhart, Ind.

[21] Appl. No.: 904,478

[22] Filed: May 10, 1978

Related U.S. Application Data

[63] Continuation-in-part of Ser. No. 753,645, Dec. 23, 1976, abandoned.

[51] Int. Cl.$^2$ .............................................. C07C 103/76
[52] U.S. Cl. .................................. 424/230; 260/559 S
[58] Field of Search ........................ 260/559 S; 424/230

[56] References Cited

U.S. PATENT DOCUMENTS

| 2,691,025 | 10/1954 | Clinton et al. | 260/559 S |
|---|---|---|---|
| 2,691,041 | 10/1954 | Clinton et al. | 260/559 S |
| 3,177,252 | 6/1965 | Thominet | 260/559 S |
| 3,219,528 | 11/1965 | Thominet | 260/559 S |
| 3,312,739 | 4/1967 | Thominet | 260/559 S |
| 3,591,634 | 6/1971 | Thominet | 260/559 S |

FOREIGN PATENT DOCUMENTS

| 1313758 | 11/1962 | France. |
| 395959 | 7/1965 | Switzerland. |
| 862721 | 3/1961 | United Kingdom. |
| 994023 | 6/1965 | United Kingdom. |

*Primary Examiner*—Arthur P. Demers
*Attorney, Agent, or Firm*—Jerome L. Jeffers

[57] ABSTRACT

Novel 3-substituted salicylamides having increased analgesic activity and prolonged analgesic activity are disclosed.

14 Claims, No Drawings

3-SUBSTITUTED SALICYLAMIDES

BACKGROUND OF THE INVENTION

1. Related Applications

This application is a continuation-in-part of co-pending application Ser. No. 753,645 filed on Dec. 23, 1976, and now abandoned.

2. Field of the Invention

This invention is related to 3-substituted salicylamides which demonstrate increased analgesic activity accompanied by a prolongation of such activity when compared with prior art compounds having similar chemical structures.

3. Prior Art

Because salicylic acid is so irritating that it can only be used externally, various derivatives of the acid have been synthesized for systemic use. In general, the derivatives synthesized comprise two main classes, namely salicylate esters, such as aspirin, obtained by substitution on the phenol group, and amides of salicylic acid, obtained by substitution on the carboxyl group, for example, amide group substitution. Both types of derivatives are referred to collectively as "salicylates" or "salicylamide" compounds.

Another class of derivatives can be prepared from the salicylates described above by substitution on the benzene ring.

The salicyl compounds are widely used as analgesics because the compounds have lower maximal effects than do the narcotic analgesics. Hence they are used extensively for pain of slight-to-moderate intensity. They have the advantage that chronic use does not lead to tolerance or addiction. Their toxicity is lower than that of more potent analgesics. Types of pain amenable to treatment with salicyl compounds are low intensity, either circumscribed or widespread in origin, and include headache, myalgia and arthralgia.

Many of the salicylates are too toxic to be employed as general analgesics; however, because of the usefulness of aspirin and other salicylates, research to discover potent-acting salicylates, with reduced toxicity is continuing. Another disadvantage of various salicylates is their short duration of activity, due to rapid biotransformation by conjugation with endogenous glucuronic acid.

U.S. Pat. No. 2,810,718 discloses salicyl compounds substituted on the phenol group and substituted on the carboxyl group by piperazyl and piperadyl moieties, having local anesthetic and fungicidal activity. $J.$ $Chem.$ $Soc.$ 1961, pp. 661–667; $J.$ $Org.$ $Chem.$, 19, 510 (1954) $J.$ $Gen.$ $Chem.$, 8, 427 (1938) and $J.$ $Org.$ $Chem.$, 2, 253–259 (1937) all merely disclose the laboratory preparation of salicyl compounds substituted on the benzene nucleus; no pharmaceutical properties are disclosed.

U.S. Pat. Nos. 2,751,410; 2,751,411; and 2,751,412 disclose 3-phenysalicylamides; U.S. Pat. No. 2,879,290 discloses analgesic compounds which are 3-[N,N-Di(-loweralkyl)carbamoyl]-2-acyloxybiphenyl; $J.$ $Am.$ $Pharm.$ $Assoc.$ $Sci.$ $Ed.$, 45, 277–81 (1956) discloses analgesic compounds which are derivatives of 3-, 4- and 5-phenylsalicylamides; $Chem.$ $Ab.$, 70, p. 28655M discloses analgesic compounds which are salicylic acid derivatives; and U.S. Pat. Nos. 3,219,528; 3,177,252; and 3,312,739 disclose 3-substituted 2-diethylaminoethyl benzamide tranquilizers.

British Pat. No. 994,023 discloses dialkylaminoethyl derivatives of salicylamides of the formula:

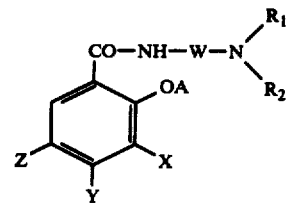

This patent further discloses that W can be $(CH_2)_2$, $R_1$ and $R_2$ can be $CH_3$, Z and Y can be H and that X can be chlorine.

SUMMARY OF THE INVENTION

The present invention is directed to 3-substituted salicylamides, having prolonged analgesic or antinociceptive activity. The salicylamides and pharmacologically acceptable, non-toxic salts thereof, are represented by the formula:

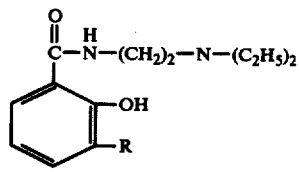

R can be; methallyl, isopropyl, allyl, t-butyl, n-butyl and isobutyl.

These compounds exhibit good analgesic activity and a longer duration of such activity when compared to structurally similar prior art compounds.

DETAILED DESCRIPTION OF THE INVENTION

The compounds described and claimed are effective in treating algia by producing an analgesic effect, i.e., reduction of pain, in an individual.

The term "individual" as utilized in this specification means a human being or an experimental animal that is a model for a human being. Medical indications for the use of the analgesics of the present invention are any conditions in which it is desired to treat algia in an individual. Although the amount will vary from individual to individual and from indication to indication, it is easily determined by one skilled in the art without undue experimentation. Dose forms for administration of the analgesic can be prepared by recognized methods in the pharmaceutical sciences.

The compounds of the present invention can be prepared by the methods described hereinafter and designated as Method A and Method B.

Method A [See $J.$ $Org.$ $Chem.$, 15, 232–236 (1950)] involves mixing together potassium carbonate and a substituted phenol in about a 2:1 to 3:1 molar ratio of carbonate/phenol, and heating in the presence of $CO_2$. The pressure can vary between about 100 and 1580 psi; the temperature can vary between about 110° and 250° C. A high yield can be obtained at a temperature of 125° for 8 hours at a pressure of about 250 psi. Pressures as low as 100 psi can be used when operating at higher temperatures, e.g. 175° C. The substituted salicylic acid formed is dissolved in hot water and unreacted phenol removed by extraction with ether. The substituted salicylic acid is obtained by precipitation with an acid, e.g., concentrated HCl. The substituted acid can be dried in an oven, or extracted with ether, dried over MgSO₄ and evaporated.

The substituted salicylic acid intermediate is then esterified in the carboxyl group by treating the acid with a mixture of absolute methanol and boron trifluoride and the reaction mixture heated to reflux [See *J. Chem. Soc.*, 577 (1965)]. The esterification can be accomplished in high yield by using about two equivalents of commercially available boron trifluoride-methanol complex in an excess of methanol, e.g., about two equivalents of the complex in an excess of about 5 volumes of methanol has been found to be satisfactory. Alternately, the esterification can be accomplished by standard organic chemical procedures involving the use of a methanol-dilute acid mixture, e.g., CH₃OH/HCl.

The reaction mixture, containing the esterified salicylate compound is then added to a saturated solution of sodium bicarbonate and extracted with an organic solvent, such as ether, dried and evaporated. The extracted salicylate, usually present as an oil, is crystallized or chromatographed by standard techniques. For example, the oil can be crystallized from methanol or can be chromatographed on silica gel.

The salicylate obtained is then converted to the desired salicylamide by refluxing with N,N-diethylethylenediamine in about a 1:1 ester/amine molar ratio. [See U.S. Pat. No. 2,810,718 and CA 52, 2918a].

The method described is shown schematically below:

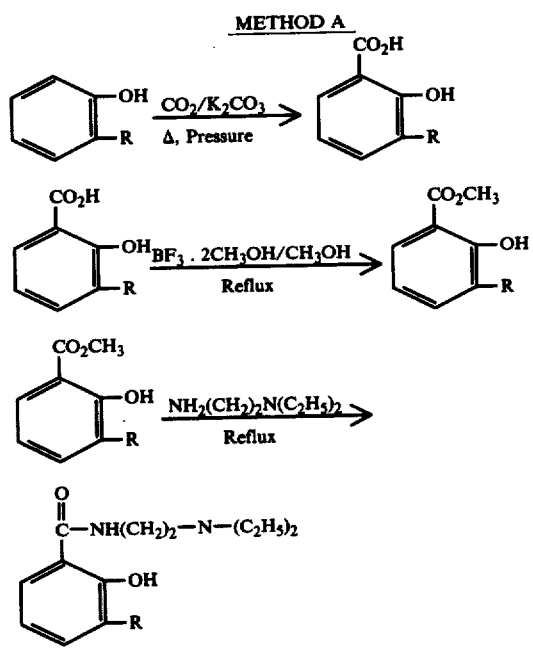

The compounds of the instant invention can also be prepared by Method B [See *J. Am. Pharm. Assoc. Sci. Ed.*, 41, 155 (1952)] which involves refluxing together a mixture of granulated sodium, a solvent such as dry xylene, and a substituted phenol while continuously bubbling carbon dioxide through the refluxing mixture. The phenol/sodium molar ratio can be from about 2:1 to 3:1. The granulated sodium is added in small amounts while the mixture is refluxing, over a period of about 1 to 3 hours, while a continual stream of dry carbon dioxide gas is bubbled into the reaction mixture. The reaction mixture is then refluxed for about 9 hours or, if convenient, overnight. After cooling, sufficient water is added slowly to destroy any excess sodium present; the substituted salicylic acid intermediate can be recovered, esterified and amidated as described in Method A hereinbefore.

The method described is shown schematically below:

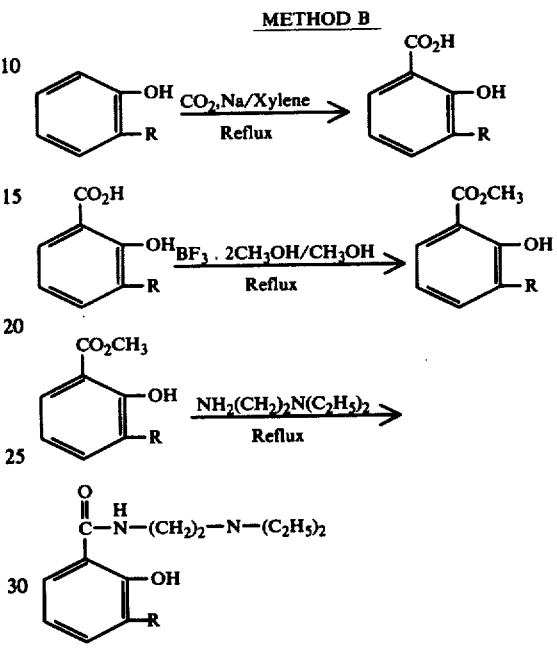

DESCRIPTION OF THE PREFERRED EMBODIMENTS

The following general example illustrates the production of a 3-substituted salicylamide by the procedure described in Method A.

GENERAL EXAMPLE

N-(2-diethylaminoethyl)-3-fluorosalicylamide hydrochloride

A mixture of 20 g (0.179 mole) 2-fluorophenol and 75 g (0.543 mole) anhydrous potassium carbonate was placed in an autoclave having a total volume of 320 ml. The autoclave was filled to the top with dry ice, sealed and heated to a temperature of about 175° for about 7 hours. The autoclave was then allowed to cool to room temperature and the solid substituted salicylic acid present in the autoclave removed by dissolving the acid in hot water. The substituted salicylic acid solution obtained was acidified with concentrated hydrochloric acid and the resulting suspension extracted with ether. The ether layer was dried over anhydrous magnesium sulfate and evaporated in vacuo to obtain 3-fluorosalicylic acid. The fluorosalicylic acid had a melting point of 133° to 135°.

A 15.6 g (0.10 mole) portion of 3-fluorosalicylic acid was dissolved in a 100 ml portion of absolute methanol. A 22 ml portion of borontrifluoride-methanol reagent (2 equivalents, 51% BF₃) was added and the reaction allowed to reflux for about six hours. The reaction mixture was cooled and added carefully to a saturated solution of sodium bicarbonate. The resulting mixture was then extracted with ether, the ether layer dried over magnesium sulfate and evaporated in vacuo. The oil obtained was crystallized from methanol. The methyl-3-fluorosalicylate obtained had a melting point of 94°-5° C.

A 5.10 gram portion of methyl-3-fluorosalicylate (0.03 mole) was refluxed with a 3.49 g portion of N,N-diethylethylenediamine (0.03 mole) for about four hours and evaporated in vacuo. The brown oil obtained was chromatographed on silica gel with ether and the desired product isolated as the hydrochloride, m.p. 108°-110° C.

Calcd. for $C_{13}H_{20}FClN_2O_2$: C, 53.69; H, 6.93; N, 9.64
Found: C, 52.58; H, 6.71; N, 9.58.

The following example illustrates production of one of the compounds of the present invention by the procedure described in Method B.

EXAMPLE 1

N-(2-diethylaminoethyl)-3-isopropylsalicylamide hydrochloride

A 13.7 gram portion (0.1 mole) of 2-isopropylphenol was added dropwise to a stirred refluxing mixture containing 4.6 grams granular sodium (0.2 mole) in 150 ml dry xylene to which a continuous stream of carbon dioxide was bubbled. For convenience, the reaction was allowed to continue overnight. After cooling the reaction mixture slightly, sufficient water was carefully added to the reaction mixuture to destroy the excess sodium and to dissolve the solids present in the reaction mixture. Acidification of the water layer with concentrated hydrochloric acid yielded a solution containing 3-isopropylsalicylic acid which was extracted with ether, dried over magnesium sulfate and evaporated in vacuo.

A 14.4 g portion of the 3-isopropylsalicylic acid (0.08 mole) and 20 ml boron trifluoride-methanol complex was dissolved in 100 ml of absolute methanol and refluxed for six hours. The ester solution obtained was poured into a saturated solution of sodium bicarbonate and the ester extracted with ether. The ether layer was dried over anhydrous magnesium sulfate and evaporated in vacuo, producing a green-colored oil.

A 13.5 gram portion of the ester was refluxed with a 8.1 gram portion of N,N-diethylethylenediamine (0.07 mole) for about four hours. The methanol formed was removed in vacuo. The light brown oil obtained was chromatographed on a silica gel column with ether. Addition of a solution of hydrochloric acid in methanol produced a white precipitate. The precipitate was recovered by filtration, dried, stirred with ethyl acetate, filtered and again dried. The product was isolated as the hydrochloride, m.p. 141°-142°.

Calcd. for $C_{16}H_{27}ClN_2O_2$: C, 61.00; H, 8.64; N, 8.89
Found: C, 61.13; H, 8.67; N, 8.99.

EXAMPLE 2

N-(2-diethylaminoethyl)-3-methylsalicylamide hydrochloride

Commercially available 3-methylsalicylic acid was esterified and amidated by the procedure described in the General Example and Example 1. Alternately, the method described in Example 1 can be used, utilizing 2-methylphenol as the starting material. After esterification and amidation, the desired product was isolated as the hydrochloride, m.p. 134°-135° C.

Calcd. for $C_{14}H_{23}ClN_2O_2$: C, 58.63; H, 8.09 N, 9.77
Found: C, 58.66; H, 8.33; N, 9.87.

EXAMPLE 3

N-(2-diethylaminoethyl)-3-n-octylsalicylamide hydrochloride

The method described in Example 1 was used to prepare the desired n-octyl-substituted salicylamide by adding a 71 g portion (0.345 mole) of 2-n-octylphenol to a stirred refluxing mixture containing 16.3 g granular sodium (0.71 mole). After esterification and amidation, the desired product was isolated as the hydrochloride, m.p. 89°-91° C.

Calcd. for $C_{21}H_{37}ClN_2O_2$: C, 65.49; H, 9.69; N, 7.28
Found: C, 66.00; H, 10.11; N, 7.26.

EXAMPLE 4

N-(2-diethylaminoethyl)-3-n-butylsalicylamide oxalate

The method described in the General Example was used to prepare the desired n-butyl-substituted salicylamide by mixing together a 15 g portion (0.10 mole) of 2-n-butylphenol and 45 g (0.325 mole) anhydrous potassium carbonate and heating in an autoclave to a temperature of about 175° for about 7 hours. After esterification and amidation, the desired product was isolated as the oxalate, m.p. 104°-106° C.

Calcd. for $C_{19}H_{30}N_2O_6$: C, 59.68; H, 7.71; N, 7.32
Found: C, 58.49; H, 7.76; N, 7.47

EXAMPLE 5

N-(2-diethylaminoethyl)-3-isobutylsalicylamide hydrochloride

The method described in the General Example was used to prepare the desired isobutyl-substituted salicylamide by mixing together a 14.0 g portion (0.093 mole) of 2-isobutylphenol and 45 g (0.325 mole) anhydrous potassium carbonate in an autoclave and heating to a temperature of about 175° for about 7 hours. After esterification and amidation, the desired product was isolated as the hydrochloride, m.p. 111°-113° C.

Calcd. for $C_{17}H_{29}ClN_2O_2$: C, 62.08; H, 8.89; N, 8.52
Found: C, 61.42; H, 9.07; N, 8.46.

EXAMPLE 6

N-(2-diethylaminoethyl)-3-t-butylsalicylamide hydrochloride

The method described in Example 1 was used to prepare the desired t-butyl-substituted salicylamide by adding a 90.0 g portion (0.60 mole) of 2-t-butylphenol to a stirred refluxing mixture containing 27.6 g granular sodium (1.20 moles). After esterification and amidation, the desired product was isolated as the hydrochloride, m.p. 139.5°-140.5° C.

Calcd. for $C_{17}H_{29}ClN_2O_2$: C, 62.08; H, 8.89; N, 8.52.
Found: C, 61.06; H, 9.01; H, 8.66.

EXAMPLE 7

N-(2-diethylaminoethyl)-3-t-amylsalicylamide hydrochloride

The method described in Example 1 was used to prepare the desired t-amyl-substituted salicylamide by adding a 98.0 g portion (0.60 mole) of 2-t-amylphenol to a stirred refluxing mixture containing 27.6 g granular sodium (1.20 moles). After esterification and amidation, the desired product was isolated as the hydrochloride, m.p. 141°-143° C.

Calcd. for $C_{18}H_{31}ClN_2O_2$: C, 63.05; H, 9.16; N, 8.22
Found: C, 61.78; H, 9.07; N, 8.42.

EXAMPLE 8

N-(2-diethylaminoethyl)-3-allylsalicylamide oxalate

The method described in the General Example was used to prepare the desired allyl-substituted salcylamide by mixing together a 13.4 g portion (0.10 mole) of 2-allylphenol and 45 g (0.325 mole) anhydrous potassium carbonate in an autoclave and heating to a temperature of about 175° for about 7 hours. After esterification and amidation, the desired product was isolated as the oxalate, m.p. 152°153° C.

Calcd. for $C_{18}H_{26}N_2O_6$: C, 59.00; H, 6.60; N, 7.64
Found: C, 58.07; H, 7.03; N, 7.87.

EXAMPLE 9

N-(2-diethylaminoethyl)-3-methallylsalicylamide oxalate

The method described in the General Example was used to prepare the desired methallyl-substituted salicylamide by mixing together a 12.0 g portion (0.081 mole) of 2-methallylphenol and 45 g (0.325 mole) anhydrous potassium carbonate in an autoclave and heating to a temperature of about 175° for about 7 hours. After esterification and amidation, the desired product was isolated as the oxalate, m.p. 105°-108° C.

Calcd. for $C_{19}H_{28}N_2O_6$: C, 59.99; H, 7.42; N, 7.36
Found: C, 59.14; H, 7.34; N, 7.09.

EXAMPLE 10

N-(2-diethylaminoethyl)-3-chlorosalicylamide hydrochloride

The method described in Example 1 was used to prepare the desired chloro-substituted salicylamide by mixing together a 12.9 g portion (0.10 mole) of 2-chlorophenol and 45 g (0.325 mole) anhydrous potassium carbonate in an autoclave and heating to a temperature of about 175° for about 7 hours. After esterification and amidation, the desired product was isolated as the hydrochloride, m.p. 143.5°-145° C.

Calcd. for $C_{13}H_{20}Cl_2N_2O_2$: C, 50.83; H, 6.56; N, 9.13.
Found: C, 51.64; H, 6.57; N, 9.35.

The starting materials used are available commercially from chemical supply houses, for example, Aldrich Chemical Co., Inc., 940 W. Saint Paul Avenue, Milwaukee, Wisconsin, 53233, or can be manufactured according to procedures described in the literature. Table I indicates whether the starting materials are commercially available, or in the alternative, lists the literature reference to the method of synthesis.

TABLE I

| | Source of Starting Phenols | |
|---|---|---|
| Example | Commercial | Literature Reference |
| General Example | Yes | |
| 1 | Yes | |
| 2 | Yes | |
| 3 | | Chem. Ab. 25, 1228 |
| 4 | | Chem. Ab. 25, 1228 |
| 5 | | By reduction of starting material of Example 10 |
| 6 | Yes | |
| 7 | Yes | |
| 8 | | J.Am.Chem.Soc. 64, 607–612 (1942) |
| 9 | | J.Am.Chem.Soc. 57, 371–376 (1935) |
| 10 | Yes | |

In order for a drug to act, it must be absorbed, transported to the appropriate tissue or organ, penetrate to the responding subcellular structure and elicit a response for a desired period of time. The pharmaceutic and therapeutic implication of these enumerated factors is that the usefulness of a drug does not depend on a single effect of the drug in question. Thus standard pharmaceutical science texts usually point out that the potency of a drug has little utility other than to provide a means of comparing the relative activities of drugs in a series to determine relative potencies. As pointed out in Remington's Pharmaceutical Sciences, Fourteenth Edition (p. 729), the potency of a drug has little bearing on its clinical usefulness provided that the potency is not so low as to cause the dosage amount to be unmanageable or to increase the treatment cost over equivalent drugs. The main consideration in governing drug choices is the selectivity of the action of the drug.

For example, assessment of an analgesic compound should include assessment of potency and relative potency, toxicity, and duration of activity.

The compounds of the present invention were investigated not only to determine their relative analgesic potency in comparison with a control salicylamide unsubstituted at the 3-position and one that was chloro, methyl, amyl or n-octyl substituted at the 3-position but also to determine the duration of analgesic activity.

The analgesic activity of the compounds of the present invention was tested in mice by means of the "abdominal constriction" response. The test is based on the observation that following interperitoneal injection of a noxious agent, such as acetylcholine chloride, mice show a response which consists of a wave of constriction and elongation passing caudally along the abdominal wall, sometimes accompanied by twisting of the trunk and followed by extension of the hind limbs. Compounds are then tested for analgesic activity by determining whether they are effective in suppressing this abdominal constriction response [See Collier et al., Br. J. Pharmac. Chemother., 32, 295–310 (1968)].

Non-fasted female mice, weighing between 20 and 25 g, were used in the studies. Compounds to be tested were administered subcutaneously at a dose of 20 mg/kg to groups of ten mice, ten minutes before the interperitoneal injection of acetylcholine chloride (3.2 mg/kg). The animals were then placed in a circular glass enclosure and the number of responses counted during a given time period.

Compounds completely inhibiting the response to acetycholine in at least five out of ten animals were subsequently tested at reduced dosage levels, using groups of ten animals per dose. The dose required to produce a specified response, that is, analgesic effect, is termed the individual effective dose; the response is a quantal rather than a graded response, since it is either present or absent. The cumulative frequency distribution of individual effective doses obtained, plotted as a function of logarithm of dose, is known as a dose-percent or dose-response curve. The $ED_{50}$ and $ED_{90}$ is then calculated from the dose-response curve obtained in the above experiments. The expression $ED_{50}$ indicates the amount of compound required to produce analgesic effect in 50 percent of animals tested and is known as the "median effective dose". The expression $ED_{90}$ indicates the amount of compound required to produce an analgesic effect in 90 percent of animals tested.

The duration of analgestic activity of the active salicylamides of the present invention was measured by determining the time necessary for 50 percent decay of the analgesic effect of the $ED_{90}$ dosage level to occur.

Experimental results obtained are shown in Table II below.

TABLE II

| | Abdominal Constriction Response | | |
|---|---|---|---|
| Example | R | ED$_{50}$ (mg/kg) | Duration of Activity ↓T (Minutes)** |
| Control* | hydrogen | 16.6 | 30 |
| 2 | methyl | 14.2 | <40**** |
| 9 | methallyl | 23.8 | 60 |
| 1 | isopropyl | 12.7 | 80 |
| 8 | allyl | 17.2 | 80 |
| 6 | t-butyl | 14.3 | 120 |
| 4 | n-butyl | 31.0 | 125 |
| 5 | isobutyl | 44.5 | 205 |
| 3*** | n-octyl | no activity | — |
| 7*** | amyl | no activity | — |
| 10*** | chloro | no activity | — |

*N-(2-diethylaminoethyl)salicylamide hydrochloride
**Pharmacologically equipotent doses administered to animals - Duration of activity based on ED$_{90}$ dosages.
***These compounds showed no analgesic activity at (20 mg/kg).
****The analgesic effects of this compounds ED$_{90}$ are practically gone 40 minutes after injection.

The experimental tests results summarized above provide the basis for the following conclusions.

All of the compounds listed above with the exception of the chloro, amyl and n-octyl derivatives, exhibited analgesic activity, including the control compound, the 3-unsubstituted salicylamide, N-(2-diethylaminoethyl)-salicylamide hydrochloride. The determination of ED$_{50}$ dosage for Examples 1, 5, 6 and 9 are, within experimental accuracy, substantially at the same potency as that of the control compound. However, the duration of activity of these representative compounds increased dramatically by a factor of up to 4-fold with substitution at the 3-position of the ring. The data indicates that the compounds of Example 4 and 5 are both less active analgesics than the other examples and the control sample, but both compounds exhibit greatly increased duration of analgesic activity in comparison to the unsubstituted control compound, by a factor of greater than 5-fold. It is further noted that the 3-chloro, amyl and n-octyl compounds showed no analgesic activity at dosages of 20 mg/kg. The methyl compound of Example 2 exhibited analgesic activity and a fairly low ED$_{50}$ but no meaningful increase in the duration of analgesic activity.

What is claimed is:

1. A compound of the formula

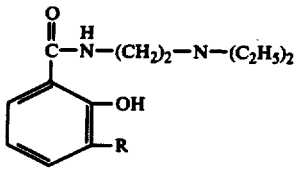

and pharmacologically acceptable, non-toxic salts thereof wherein:

R is a member selected from the group consisting of methallyl, isopropyl, allyl, t-butyl, n-butyl, and isobutyl.

2. A compound as claimed in claim 1, wherein R is methallyl.

3. A compound as claimed in claim 1, wherein R is isopropyl.

4. A compound as claimed in claim 1, wherein R is allyl.

5. A compound as claimed in claim 1, wherein R is t-butyl.

6. A compound as claimed in claim 1, wherein R is n-butyl.

7. A compound as claimed in claim 1, wherein R is isobutyl.

8. A therapeutic method for treating algia in an individual for whom such therapy is indicated comprising: administering to the individual an effective analgesic amount of a compound of the formula

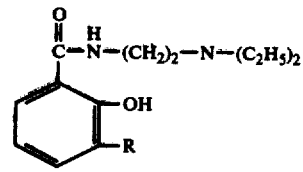

or pharmacologically acceptable, non-toxic salts thereof wherein:

R is a member selected from the group consisting of methallyl, isopropyl, allyl, t-butyl, n-butyl and isobutyl.

9. A method as claimed in claim 8, wherein R is methallyl.

10. A method as claimed in claim 8, wherein R is isopropyl.

11. A method as claimed in claim 8, wherein R is allyl.

12. A method as claimed in claim 8 wherein R is t-butyl.

13. A method as claimed in claim 8, wherein R is n-butyl.

14. A method as claimed in claim 8, wherein R is isobutyl.

* * * * *